United States Patent [19]

Takahashi

[11] Patent Number: 4,616,631

[45] Date of Patent: Oct. 14, 1986

[54] FLEXIBLE PIPE ASSEMBLY FOR ENDOSCOPE

[75] Inventor: Nagashige Takahashi, Tokyo, Japan

[73] Assignee: Kabushiki Kaisha Medos Kenkyusho, Tokyo, Japan

[21] Appl. No.: 371,168

[22] Filed: Apr. 23, 1982

Related U.S. Application Data

[63] Continuation of Ser. No. 117,416, Jan. 31, 1980, abandoned.

[30] Foreign Application Priority Data

Feb. 10, 1979 [JP] Japan .............................. 54-16206[U]

[51] Int. Cl.4 ............................................... A61B 1/06
[52] U.S. Cl. ....................................................... 128/6
[58] Field of Search .................................... 128/4–8; 138/103

[56] References Cited

U.S. PATENT DOCUMENTS

| 1,303,135 | 5/1919 | Wappler | 128/7 |
| 2,599,662 | 6/1952 | Rosenbaum | 128/6 |
| 3,496,931 | 2/1970 | Pilling | 128/6 |
| 3,945,375 | 3/1976 | Banko | 128/6 |
| 3,961,647 | 6/1976 | Doubleday | 138/103 |

FOREIGN PATENT DOCUMENTS 2805451 8/1978 Fed. Rep. of Germany .......... 128/6

Primary Examiner—Edward M. Coven
Assistant Examiner—Max F. Hindenburg
Attorney, Agent, or Firm—Sughrue, Mion, Zinn, Macpeak, and Seas

[57] ABSTRACT

A flexible pipe assembly for an endoscope including a body of flexible material having both hollow grooves with side walls formed in outer wall portions thereof and cylindrical through-holes formed in a central portion of the body both of which extend along the axis of the body. Channel forming pipes are laterally arranged in any of the hollow grooves and cylindrical through-holes. The channel forming pipes may be bundled together to prevent them from being twisted. Various tube members such as multi-purpose tubes having plural channels which can convey air, water and suction as well as optical and electrical conductors may be positioned in the hollow grooves.

9 Claims, 5 Drawing Figures

FLEXIBLE PIPE ASSEMBLY FOR ENDOSCOPE

This is a continuation of application Ser. No. 117,416 filed Jan. 31, 1980 now abandoned.

BACKGROUND OF THE INVENTION

The present invention relates to a flexible pipe assembly of an endoscope which is designed to be inserted into a body cavity and to a flexible pipe assembly which is connected between the manual operating section of the endoscope and an external device or the like. A specific feature of the invention resides in the arrangement of the flexible pipe assembly in which channel forming pipes used for various purposes are arranged to be bundled together and to be removed when necessary.

Since the introduction of the endoscope for various medical examination and medical treatment purposes, a variety of optical and electrical elements have been proposed for the endoscope. These elements are designed to be extended through channels in the endoscope to designated points in the body cavity and to external devices through the manual operating section of the endoscope.

If a number of such channels are simply bundled together to a flexible pipe assembly which is to be inserted into the body cavity, then a number of spaces must be formed between the channel forming pipes. Accordingly, it is necessary to use an outer pipe having a relatively large diameter to cover all the bundled channel forming pipes. Thus, the assembly of the pipes has a low flexibility with the result that it is difficult to insert the pipe assembly into the body cavity. That is, because of this, the performance of the endoscope with the pipe assembly is lowered. Furthermore, if the outer pipe or the water supplying channel tube is broken, the other channel forming pipes may be adversely affected and the inside of the outer pipe may be contaminated.

In order to eliminate the above-described difficulties which are due to the use of channel forming pipes which have been simply bundled together as described above, the following two techniques have been proposed in the art. In a first one of the two techniques, as disclosed in Japanese Utility Model Publication No. 27116/1973 the channel forming pipes for the aforementioned elements are bundled together and are then molded with synthetic resin. In the other technique as disclosed in Japanese Laid-Open Utility Model Application No. 111591/1978 a flexible pipe is employed which has hollow parts serving as channel forming pipes and hollow parts into which channel forming pipes are inserted.

An endoscope of this type uses elements such as a bundle of optical fibers and electrical conductors which are relatively high in durability but also elements such as an air supplying pipe, a water supplying pipe and a suction pipe which are susceptible to damage and must be frequently inspected and cleaned. Accordingly, in the above-described conventional technique in which the channel forming pipes for these elements are bundled together and are then molded or the channel forming pipes are inserted into the hollow parts to form one pipe assembly, the bundling effect may be expected. However, if the suction pipe is clogged up for instance, it is rather difficult to eliminate the trouble and it may be necessary to replace the entire flexible pipe assembly.

Accordingly, an object of the invention is to provide a flexible pipe assembly for an endoscope in which the channel forming pipes can be sufficiently bundled together and, among the channel forming pipes, one to several channel forming pipes can be readily removed from the assembly.

SUMMARY OF THE INVENTION

These, as well as other objects of the invention, may be met by a flexible pipe assembly for an endoscope including a body of flexible material having hollow grooves with side walls formed in outer wall portions of the body and cylindrical through-holes formed in a central portion of the body wherein the hollow grooves and cylindrical through-holes extend along the longitudinal axis of the body and channel forming elements adapted to be disposed in at least some of the hollow grooves and cylindrical through-holes.

DESCRIPTION OF THE PREFERRED EMBODIMENTS

The invention will be described in detail with reference to its preferred embodiments shown in the accompanying drawing.

Figure 1:
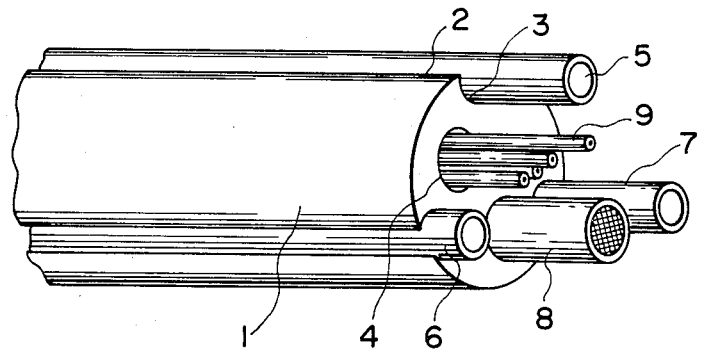
FIG. 1 is a perspective view with parts cut away showing an example of a flexible pipe assembly according to the invention.
Figure 2:
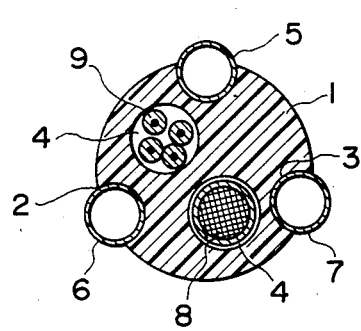
FIG. 2 is a cross-sectional view of the assembly shown in FIG. 1.

FIG. 1 is a perspective view, with parts cut away, of an example of a flexible pipe assembly according to the invention and FIG. 2 is a cross-sectional view thereof. A rod-shaped body 1 is made of a flexible material such as rubber or plastic resin. The outer wall portion of the body is cut along the axis to form several hollow grooves 3 with side walls 2 which extend longitudinally. Furthermore, several cylindrical through-holes 4 are formed in the central portion of the body 1 also extending longitudinally. An air supplying tube 5 is positioned on one of the hollow grooves 3 and a water supplying tube 6 and a suction tube 7 are inserted into the remaining two hollow grooves 3. A bundle of optical fibers 8 and a bundle of electrical conductors 9 are inserted into the cylindrical through-holes 4.

In inserting the tubes, which are channel forming tubes, into the respective hollow grooves 3, the side walls 2 of the hollow groove 3 are pushed aside by the tube against the elastic force of the material of the body 1 so that the tube is fitted into the groove. The bundle of electrical conductors is inserted into its respective cylindrical through-holes through its opening at one end of the body 1.

Figure 3:
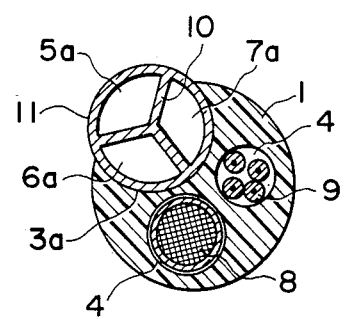
FIGS. 3 through 5 are cross-sectional views of other examples of a flexible pipe assembly constructed according to the invention.

FIG. 3 is a sectional view showing another example of the flexible pipe assembly according to the invention. Cylindrical through-holes 4 and 4 are formed in the central portion of a body 1 and a hollow groove 3a larger than that shown in FIG. 2 is formed in the outer wall portion of the body 1. A multi-purpose tube 11 composed of an air supplying channel 5a, a water supplying channel 6a and a suction channel 7a, which are separated from one another by partitions 10, is fitted in the hollow groove 3a.

Figure 4:
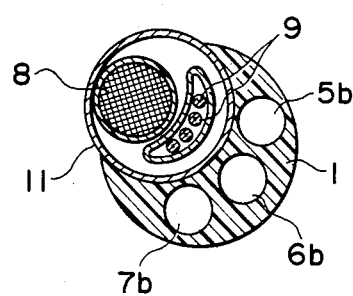

The arrangement of the flexible pipe assembly shown in FIG. 3 may be modified as shown in FIG. 4 by changing the arrangement of the multi-purpose tube 11 and the cylindrical through-holes 4. More specifically, the cylindrical through-holes 4 in the body 1 are used as an air supplying channel 5b, a water supplying channel 6b and a suction channel 7b, respectively. The bundles of optical fibers 8 and the electrical conductors 9 are inserted into the multi-purpose tube 11.

Figure 5:
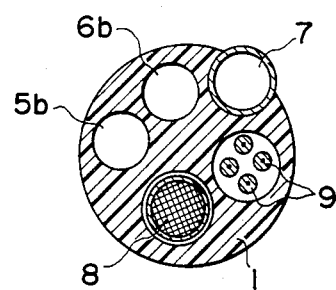

In practice, it may be desirable to discard the suction tube 7 after use. Therefore, the flexible pipe assembly may be modified as shown in FIG. 5. Only the suction tube 7 is fitted in the hollow groove 3 and two of the cylindrical through-holes are used as the air supplying channel 5b and the water supplying channel 6b while the bundle of optical fibers 8 and the bundle of electrical conductors 9 are inserted into the remaining cylindrical through-holes 4.

The body 1 of the flexible pipe assembly thus constructed can be readily formed with a simple technique such as extrusion molding. The channel elements mentioned above can be arranged in the body 1 by press-fitting or inserting them in the manner described above. The tubes fitted in the hollow grooves 3 can be readily removed by pulling them in a manner opposite to the manner employed in fitting. In other words, the tubes held in the hollow groove 3 by force of the elasticity of the material of the body or by the elastic force of the side walls 2 of the hollow grooves 3 can be readily removed from the body 1 simply by pulling them out.

In order to effectively press-fit the tubes into the hollow grooves or to remove them therefrom, it is necessary to suitably determine the distance between the side walls 2 of each hollow groove according to the elasticity of the material of the body and the diameter of the tube to be inserted into the hollow groove 3. That is, the distance between the two side walls 2 should be selected so that, under the condition that about more than a half of the circumference of the tube is in the hollow groove 3, the edge portions of the side walls are in contact with the outer wall of the tube. In the examples of the flexible pipe assembly described above, the diameters of the grooves and the cylindrical through-holes are selected so that the inner walls thereof are in close contact with the outer walls of the tubes inserted thereinto. However, the invention is not limited thereto or thereby. That is, the diameters may be such that the tubes are loose-fitted.

As is clear from the above description, the flexible pipe assembly according to the invention has hollow grooves with side walls which are formed in the outer wall portions of the body and cylindrical through-holes formed in the central portion of the body. That is, the flexible assembly has two kinds of channel forming pipe accommodating means. The channel forming pipes can be readily arranged in the hollow grooves and the cylindrical through-holes. Furthermore, if the channel forming pipes are bundled together, then it is possible to prevent the channel forming pipes from being twisted. The flexible pipe assembly according to the invention is advantageous in that the space occupied by the pipe bundles is minimized, the diameter of the assembly is also minimized, and the assembly itself is sufficiently flexible. Since the channel forming pipe fitted into the hollow groove with the side walls can be readily removed from the body, the channels can be suitably inspected and cleaned. In addition to the above-described advantageous effects, the fact that the channel forming pipes can be readily inserted into and removed from the body so that the channel forming pipes can be readily repaired and can be discarded after used should be highly appreciated in practical use.

What is claimed is:

1. An endoscope comprising: an elongate body having an axis extending along its length of flexible material having at least one hollow groove having side walls formed in outer wall portions of said body and an opening extending the length of said elongate body and cylindrical through-holes formed in the central portion of said body wherein said hollow grooves and said cylindrical through-holes extend parallel to the axis of said body; a channel forming element disposed in at least one of said hollow grooves and said cylindrical through holes and being strippable from said grooves along said opening and, endoscopic implements delivered through said channel forming elements.

2. The endoscope of claim 1 further comprising a multi-purpose tube having a plurality of channels formed therein separated by partitions, said multi-purpose tube being positioned in one of said hollow grooves formed in outer wall portions of the said body and having endoscopic implements delivered therethrough.

3. The endoscope of claim 2 further comprising: said multi-purpose tube having at least one hollow channel formed therein, a channel for bundled members formed therein and, bundled members placed in said channel.

4. The endoscope of claim 3 where said bundled members comprise: electrical conductors.

5. The endoscope of claim 3 wherein said bundled members comprise: optical fibers.

6. The endoscope of claim 1 further comprising: a bundle of optical fibers positioned in one of said cylindrical through-holes and a bundle of electrical conductors positioned in another one of said cylindrical through-holes.

7. The endoscope of any of claims 1, 2, 3, 4, 5 or 6 wherein said side walls of said hollow grooves have a partially cylindrical shape.

8. An endoscope comprising: an elongate body having an axis extending along its length of flexible material having at least one hollow groove having side walls formed in outer wall portions of said body and an opening extending along the length of said body, cylindrical through-holes formed in the central portion of said body wherein said hollow groove and said cylindrical through-holes extend parallel to the axis of said body; a first channel-forming element adapted to be press fitted into said hollow groove through said opening by flexing said elongate body, and a second channel-forming element inserted into a cylindrical through-hole and, endoscopic implements delivered through said channel-forming elements.

9. An endoscope comprising: an elongate body having an axis extending along its length of flexible material having at least one hollow groove with an axially extending opening and having side walls formed in outer wall portions of said body and a cylindrical through-hole formed in the central portion of said body wherein said hollow groove and said cylindrical through-hole extend extends parallel to the axis of said body; a first channel-forming element adapted to be inserted in said hollow groove by press fitting in said opening and stripped out of said groove along said opening by flexing said body and a second channel-forming element inserted in said cylindrical through-hole and, endoscopic implements delivered through said channel-forming elements.

* * * * *